(12) United States Patent
Calvosa et al.

(10) Patent No.: US 8,663,101 B2
(45) Date of Patent: Mar. 4, 2014

(54) SURGICAL INSTRUMENT FOR OPERATIONS ON THE SPINAL COLUMN

(75) Inventors: Giuseppe Calvosa, Pisa (IT); Miria Tenucci, Lucca (IT); Renato Casella, Vecchiano (IT)

(73) Assignee: N.B.R. New Biotechnology Research, Verona (IL)

(*) Notice: Subject to any disclaimer, the term of this patent is extended or adjusted under 35 U.S.C. 154(b) by 181 days.

(21) Appl. No.: 12/812,490

(22) PCT Filed: Nov. 20, 2009

(86) PCT No.: PCT/EP2009/065558
§ 371 (c)(1),
(2), (4) Date: Oct. 20, 2010

(87) PCT Pub. No.: WO2010/057979
PCT Pub. Date: May 27, 2010

(65) Prior Publication Data
US 2011/0028930 A1    Feb. 3, 2011

(30) Foreign Application Priority Data
Nov. 21, 2008   (IT) .............................. MI2008A2078

(51) Int. Cl.
*A61B 1/32*    (2006.01)
(52) U.S. Cl.
USPC ........................... 600/210; 600/235; 600/201
(58) Field of Classification Search
USPC .................................. 600/201–249; 433/141
See application file for complete search history.

(56) References Cited

U.S. PATENT DOCUMENTS

| 2,473,266 | A | * | 6/1949 | Wexler | 600/215 |
|---|---|---|---|---|---|
| 2,666,428 | A | * | 1/1954 | Glenner | 600/210 |
| 2,863,444 | A | * | 12/1958 | Winsten | 600/214 |
| 3,766,910 | A | * | 10/1973 | Lake | 600/213 |
| 4,610,243 | A | * | 9/1986 | Ray | 600/206 |
| 4,686,972 | A | | 8/1987 | Kurland | |
| 5,217,463 | A | | 6/1993 | Michael | |
| 6,325,827 | B1 | | 12/2001 | Lin | |
| 6,500,206 | B1 | * | 12/2002 | Bryan | 623/17.16 |
| 7,442,195 | B1 | | 10/2008 | Behrens | |
| 2007/0043265 | A1 | | 2/2007 | Rochetin | |
| 2007/0276406 | A1 | | 11/2007 | Mahoney | |
| 2009/0036927 | A1 | | 2/2009 | Vestgaarden | |

FOREIGN PATENT DOCUMENTS

JP    2005296562 A  * 10/2005

OTHER PUBLICATIONS

PCT/EPO, International Search Report, Feb. 3, 2010.
Department of Economic Development of Italy, Research Report, Nov. 3, 2009.

* cited by examiner

*Primary Examiner* — Matthew Lawson
*Assistant Examiner* — Si Ming Lee
(74) *Attorney, Agent, or Firm* — Themis Law

(57) ABSTRACT

A surgical kit for operations on the spinal column includes a surgical instrument having a handle body, the handle body having a substantially flat portion blended with the body, wherein the substantially flat portion is shaped to urge the gauze for draining a wound.

7 Claims, 2 Drawing Sheets

SURGICAL INSTRUMENT FOR OPERATIONS ON THE SPINAL COLUMN

TECHNICAL FIELD

The present invention relates to a surgical kit for operations on the spinal column. More particularly, the present invention relates to a surgical kit that allows exposing portions of spinal column on which for example prostheses or screws are to be implanted subsequently.

BACKGROUND ART

As it is known, operations on the spinal column, particularly for implanting prostheses, screws and the like, require parting the muscles from the spinal column by using a periosteal elevator, which enables a surgeon to cut a muscle closely in contact with the spinal column so as to be able to then part it completely from the column.

In this manner, the muscle bundles separately from the spinal column, enabling the surgeon to have free access to the spinal column in order to implant fixation screws, prostheses and the like.

Currently, the technique for parting muscles from the spinal column entails using a scalpel to cut the muscles at the region of contact of the muscles with the spinal column and the periosteal elevator to separate the muscles from the bone.

This procedure is highly invasive, since parting of the muscles by resecting and separating entails considerable bleeding.

SUMMARY OF THE INVENTION

An object of the present invention is to provide a surgical kit for operations on the spinal column that enables the surgeon to part easily the muscles from the spinal column while minimizing bleeding.

A further object of the present invention is to provide a surgical kit for operations on the spinal column that enables the surgeon, with a combined action of his hands, to avoid the use of the periosteal elevator, except in the initial step, for parting the muscles from the spinal column.

Another object of the present invention is to provide a surgical kit that is highly reliable, relatively simple to provide and has a competitive cost.

These objects and others which will become better apparent hereinafter are achieved by a surgical kit for operations on the spinal column, which includes at least one elongated gauze and one surgical instrument, said surgical instrument having a handle body, said handle body having a substantially flat portion blended with said body, wherein said substantially flat portion is so shaped to urge said gauze for draining a wound.

Advantageously, there is also provided a surgical method for operations on the spinal column that is based on the surgical kit described hereinabove and that includes the following steps:

making a slit in the back of a patient proximate to the spinal column so as to divide a first muscle portion around the spinal column into a pair of separate side muscle portions; and detaching at least one of said separate side muscle portions from the spinal column, wherein said detaching includes a force-fitted insertion of at least one elongate gauze member into said slit and compression of said gauze member between the spinal column and said at least one of said side muscle portion such to controllably detach an additional separate muscle portion of said at least one of said side muscle portions from the spinal column.

BRIEF DESCRIPTION OF THE DRAWINGS

Further characteristics and advantages of the invention will become better apparent from the following detailed description of some preferred but not exclusive embodiments of the surgical kit according to the invention, illustrated by way of non-limiting examples in the accompanying drawings, wherein.

DETAILED DESCRIPTION OF EMBODIMENTS OF THE INVENTION

Figure 1:
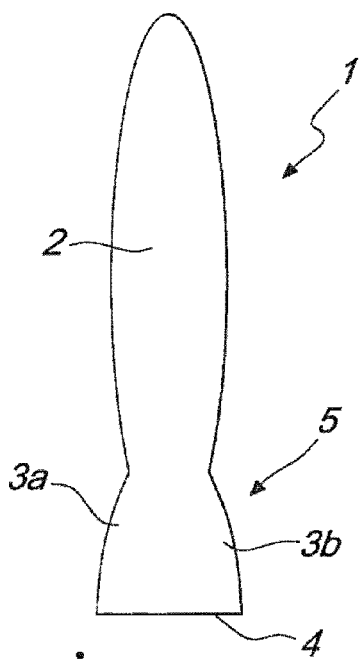
FIG. 1 is a perspective view of a first embodiment of the a surgical instrument, which is a component of the surgical kit according to the invention.
Figure 2:
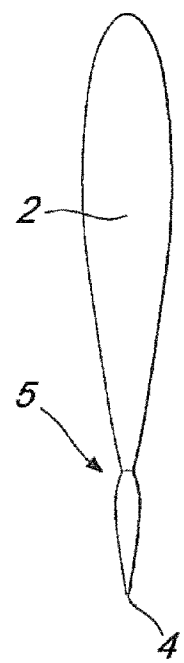
FIG. 2 is a side view of the surgical instrument of FIG. 1.

With reference to the figures, the surgical kit according to the present invention includes a surgical instrument, generally designated by the reference numeral 1, which comprises a handle 2 constituted by a plate-like body that has a substantially curved or rectilinear shape and which ends at one end with a portion that has two curvilinear parts 3a, 3b blending with the body portion, laterally thereto, and ending substantially with a flat portion 4 that blends the two curvilinear parts 3a, 3b.

In a side view, the end portion, generally designated by the reference numeral 5, has a substantially wedge-like shape and tapers toward the portion that lies furthest from the handle 2.

Figure 3:
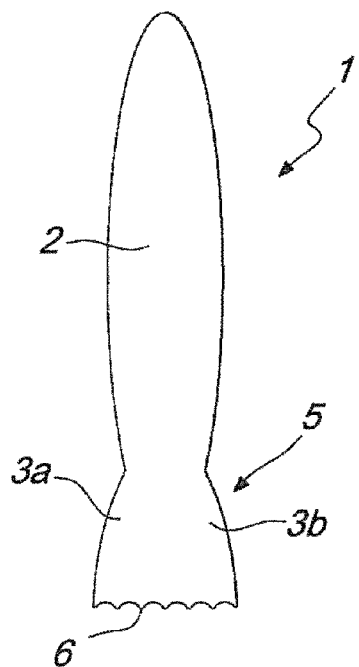
FIG. 3 is a perspective view of a second embodiment of a surgical instrument, which is a component of the surgical kit according to the invention.

Conveniently, the rectilinear portion 4 can have a set of teeth 6, as shown in FIG. 3.

Figure 4:
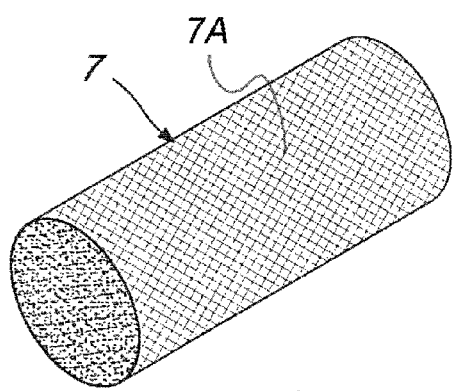
FIG. 4 is a perspective view of a gauze member, which is a further component of the surgical kit according to the invention.

The surgical instrument according to the invention is configured to be used to rotate gauzes 7 of a cylindrical shape, as shown in FIG. 4, which have different sizes and which are adapted to roll on the bone, thus parting and separating the overlying muscles "M" by pushing such muscles away from the spinal column "SC".

In detail, the surgical instrument 1 enables a surgeon to insert the gauze 7, or any cylindrical support on which a gauze is rolled, pushing it within the slit created by a scalpel and/or a periosteal elevator during the resection of the muscles "M" of the spinal column "SC", and to then push the gauze 7 downward, such to part the muscles "M" from the remaining part of the spinal column "SC", acting directly with the surgical instrument 1 and without the aid of the scalpel and/or periosteal elevator.

In a method according to the invention, the surgeon, by acting with the surgical instrument 1, pushes the gauze 7 downward, adjacently to the spinal column and between the column and the muscles to be parted, thus parting the remaining portion of muscles "M" that had not been parted beforehand by the action of the scalpel.

Figure 5:
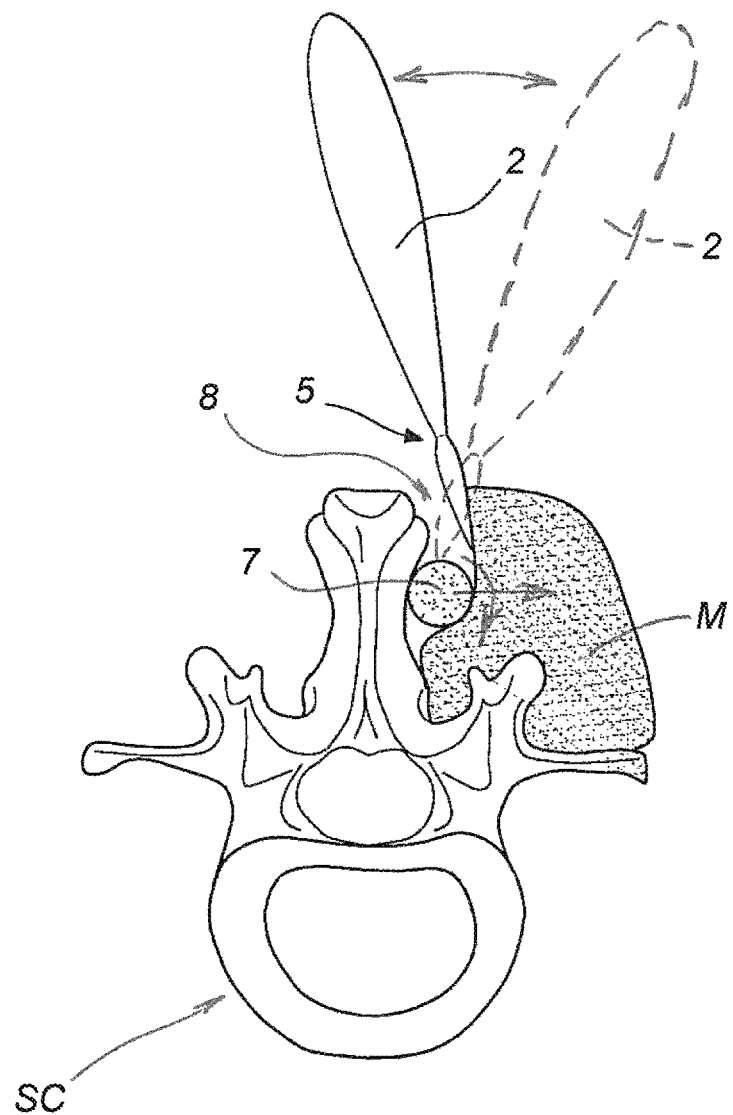
FIG. 5 shows the operating sequence of use of the surgical kit according to the present invention.

This operation can be performed more easily by using two surgical instruments according to the invention simultaneously, one held in each hand, and by performing a combined and alternating action of the two instruments, such to push the gauze 7 within the slit 8 created by the scalpel (FIG. 5).

The ability to insert the gauze 7 directly in the slit 8 created by the action of the scalpel by means of a surgical instrument 1 according to the invention enables a surgeon to part the muscles "M" from the bone and absorb most of the exiting blood due to the parting of the muscles "M" from the spinal column "SC". At the same time hemostasis can be performed by direct compression and by indirect action, thanks to the substances with which the gauze 7 can be impregnated, i.e., platelet gel, fibrin glue or other hemostatic substance.

In this manner, this step of the surgical operation is far easier to perform for the surgeon and substantially less invasive for the patient.

In practice, it has been found that the surgical instrument according to the present invention fully achieves the intended aim and objects, since it allows parting of the muscles "M" from the spinal column "SC" by using the scalpel only initially, subsequently resorting to a mechanical action of pushing the gauze 7 into the slit 8 created by the scalpel.

The novel surgical instrument 1 and the gauze 7 are susceptible of numerous modifications and variations, all of which are within the scope of the appended claims. All the features thereof may also be replaced with other technically equivalent elements.

In practice, the materials used, as well as the contingent shapes and dimensions, may be any according to intended requirements and to the state of the art.

What is claimed is:

1. A surgical kit for an operation on the human spinal column comprising, as separate and detached components:
   a cylindrical gauze, and
   a surgical instrument comprising,
      a handle body, and
      a wedge-shaped portion extending from said handle body and attached to said handle body at a common joining surface, said wedge-shaped portion having a longitudinally tapered cross-section with a decreasing thickness in a direction opposite to said common joining surface, and a transversally rectilinear end at a position opposite to the handle body,
   wherein the wedge-shaped portion is shaped to rotate the gauze between a spinal column and a muscle couple thereto.

2. The surgical kit of claim 1, wherein said wedge-shaped portion comprises lateral curved surfaces shaped to extend inwardly toward a common junction line with the handle body.

3. The surgical kit of claim 1, wherein the body comprises an elongated member with opposing convex surfaces.

4. The surgical of claim 1, wherein the transversally rectilinear end has a plurality of teeth designed to engage by contact an outer surface of the gauze for pushing the gauze into a wound slit in a back of a patient along the spinal column.

5. The surgical kit of claim 1, wherein the wedge-shaped portion has upper and lower convex surfaces.

6. The surgical kit of claim 5, wherein the handle body has a wedge-shaped portion with convex upper and lower surfaces tapering toward said common joining surface joining the wedge-shaped portion extending from the handle body.

7. The surgical kit of claim 1, wherein the cylindrical gauze is a cylindrical roll of gauze.

* * * * *